(12) United States Patent
Mesibov et al.

(10) Patent No.: US 11,096,732 B2
(45) Date of Patent: Aug. 24, 2021

(54) HYBRID BONE FIXATION WIRE (71) Applicant: GLW, Inc., Waxhaw, NC (US)

(72) Inventors: Rachael Alia Mesibov, Tappan, NY (US); Thomas Hoon Lee, Columbus, OH (US)

(73) Assignee: GLW, Inc., Englewood Cliffs, NJ (US)

( * ) Notice: Subject to any disclaimer, the term of this patent is extended or adjusted under 35 U.S.C. 154(b) by 59 days.

(21) Appl. No.: 16/795,101

(22) Filed: Feb. 19, 2020

(65) Prior Publication Data
US 2020/0268424 A1 Aug. 27, 2020

Related U.S. Application Data (60) Provisional application No. 62/808,530, filed on Feb. 21, 2019.

(51) Int. Cl.
*A61B 17/86* (2006.01)

(52) U.S. Cl.
CPC .......... *A61B 17/864* (2013.01); *A61B 17/866* (2013.01)

(58) Field of Classification Search
CPC ... A61B 17/848; A61B 17/86; A61B 17/8625; A61B 17/864; A61B 17/866; A61B 17/8685
See application file for complete search history.

(56) References Cited

U.S. PATENT DOCUMENTS

| | | | |
|---|---|---|---|
| 2,760,488 A * | 8/1956 | Pierce | A61B 17/683 606/310 |
| 6,719,759 B2 | 4/2004 | Beger et al. | |
| 7,517,350 B2 * | 4/2009 | Weiner | A61B 17/8605 606/105 |
| 7,840,254 B2 | 11/2010 | Glossop | |
| 8,979,889 B2 | 3/2015 | Geist et al. | |
| 9,089,378 B2 | 7/2015 | Riemer et al. | |
| 9,649,138 B2 | 5/2017 | Altarac et al. | |
| 9,750,551 B1 | 9/2017 | Nichols | |
| 9,795,412 B2 * | 10/2017 | Sinha | A61B 17/68 |
| 10,136,929 B2 | 11/2018 | Fallin et al. | |

(Continued)

FOREIGN PATENT DOCUMENTS

| | | |
|---|---|---|
| CN | 107645937 | 1/2018 |
| EP | 2129311 | 4/2012 |

(Continued)

OTHER PUBLICATIONS

International Searching Authority. Invitation to Pay Additional Fees for PCT application No. PCT/US2020/018834, dated Jun. 12, 2020, pp. 1-9.

*Primary Examiner* — Eric S Gibson
(74) *Attorney, Agent, or Firm* — MacMillan, Sobanski & Todd, LLC (57) ABSTRACT

Various bone fixation wires and methods of making bone fixation wires are described. A bone fixation wire includes an elongate member defining an outer wall, a retaining member disposed on the outer wall between the elongate member first end and the geometric midpoint of the axial length of the elongate member on the lengthwise axis, and a stopping member disposed on the elongate member and contacting the retaining member. The elongate member comprises a first material and the stopping member comprises a second material that is different from the first material.

20 Claims, 5 Drawing Sheets

(56) References Cited

U.S. PATENT DOCUMENTS

| | | | |
|---|---|---|---|
| 2003/0149436 A1* | 8/2003 | McDowell | A61B 17/8605 |
| | | | 606/916 |
| 2004/0097941 A1* | 5/2004 | Weiner | A61B 17/685 |
| | | | 606/312 |
| 2011/0046632 A1 | 2/2011 | Quevedo | |
| 2011/0066194 A1 | 3/2011 | Deffenbaugh et al. | |
| 2013/0079776 A1* | 3/2013 | Zwirkoski | A61B 17/848 |
| | | | 606/62 |
| 2014/0074102 A1* | 3/2014 | Mandeen | A61B 17/1764 |
| | | | 606/93 |
| 2015/0327975 A1 | 11/2015 | Euteneuer et al. | |
| 2017/0319251 A1 | 11/2017 | Viart et al. | |
| 2020/0268424 A1* | 8/2020 | Mesibov | A61B 17/866 |

FOREIGN PATENT DOCUMENTS

| | | |
|---|---|---|
| EP | 2731521 | 5/2014 |
| WO | WO2008060825 | 5/2008 |
| WO | WO2011031495 | 3/2011 |
| WO | WO2016080922 | 5/2016 |
| WO | WO2016080923 | 5/2016 |
| WO | WO2016144272 | 9/2016 |

\* cited by examiner

HYBRID BONE FIXATION WIRE

CROSS REFERENCE TO RELATED APPLICATION

This application claims the benefit of U.S. Provisional Application No. 62/808,530, filed on Feb. 21, 2019, which is hereby incorporated by reference into this disclosure in its entirety.

FIELD

The disclosure relates to the field of medical devices. More particularly, the disclosure relates to the field of orthopedic medical devices. Specific examples relate to bone fixation wires. The disclosure also relates to methods of making a bone fixation wire.

BACKGROUND

Various bone fixation wires (sometimes referred to as "K-wires" or "Kirschner wires") for use during orthopedic and related procedures are known in the art. For example, some conventional bone fixation wires define a structural feature that interacts with orthopedic plates to prevent the wire from passing too far into the opening of the plate. These wires have several drawbacks, however. For example, these wires are typically machined from rod stock of a single material, which creates significant waste in the manufacturing process, limits the relative geometries of the rod and bead portions of the wires, and produces bone fixation wires with undesirable balance and handling characteristics.

A need exists, therefore, for improved bone fixation wires and methods of making bone fixation wires.

BRIEF SUMMARY OF SELECTED EXAMPLES

Various example bone fixation wires and methods of making bone fixation wires are described herein.

An example bone fixation wire comprises an elongate member defining an outer wall, a retaining member disposed on the outer wall between the elongate member first end and the geometric midpoint of the axial length of the elongate member on the lengthwise axis, and a stopping member disposed on the elongate member and contacting the retaining member. The elongate member comprises a first material and the stopping member comprises a second material that is different from the first material.

Another example bone fixation wire comprises an elongate member having an elongate member first end defining a tip, an elongate member second end, and a lengthwise axis extending between the elongate member first end and the elongate member second end, the elongate member defining an outer wall extending between the elongate member first end and the elongate member second end; a first retaining member disposed on the elongate member outer wall between the elongate member first end and the geometric midpoint of the axial length of the elongate member on the lengthwise axis, the retaining member defining a first outer diameter; and a stopping member disposed on the elongate member and contacting the retaining member, the stopping member having a stopping member first end, a stopping member second end, a stopping member outer surface, and a stopping member inner surface, the stopping member inner surface contacting the elongate member outer surface and defining a stopping member inner lumen having an inner diameter. The elongate member comprises a first material the stopping member comprises a second material that is different from the first material.

Another example bone fixation wire comprises an elongate member having an elongate member first end defining a tip, an elongate member second end, and a lengthwise axis extending between the elongate member first end and the elongate member second end, the elongate member defining an outer wall extending between the elongate member first end and the elongate member second end, the outer wall defining a first depression disposed on the elongate member outer wall between the elongate member first end and the geometric midpoint of the axial length of the elongate member on the lengthwise axis; and a stopping member disposed on the elongate member, the stopping member having a stopping member first end, a stopping member second end, a stopping member outer surface, and a stopping member inner surface, the stopping member inner surface contacting the elongate member outer surface and defining a protrusion extending into the depression. The elongate member comprises a first material the stopping member comprises a second material that is different from the first material.

Another example bone fixation wire comprises an elongate member having an elongate member first end defining a tip, an elongate member second end, and a lengthwise axis extending between the elongate member first end and the elongate member second end, the elongate member defining an outer wall extending between the elongate member first end and the elongate member second end; the outer wall defining a first depression and a second depression, each of the first depression and the second depression disposed between the elongate member first end and the geometric midpoint of the axial length of the elongate member on the lengthwise axis, the first depression disposed opposite the second depression with respect to the lengthwise axis of the elongate member; and a stopping member disposed on the elongate member, the stopping member having a stopping member first end, a stopping member second end, a stopping member outer surface, and a stopping member inner surface, the stopping member inner surface contacting the elongate member outer surface and defining a first protrusion extending into the first depression and a second protrusion extending into the second depression. The elongate member comprises one of a metal and a metal alloy and the stopping member comprises a polymeric material.

Additional understanding of the inventive bone fixation wires and methods of making bone fixation wires can be obtained by reviewing the detailed description of selected examples, below, with reference to the appended drawings.

DETAILED DESCRIPTION OF SELECTED EXAMPLES

The following detailed description and the appended drawings describe and illustrate various example bone fixation wires and methods of making bone fixation wires. The description and drawings are provided to enable one skilled in the art to make and use an example bone fixation wire in accordance with the invention and to perform the example methods of making in accordance with the invention. They are not intended to limit the scope of the claims in any manner.

As used herein, the term "circumferential," and grammatically related terms, refers to a structural arrangement of one structure relative to another structure, feature, or property of another structure. The term does not require any specific dimensions, relative dimensions, configuration, or regularity of either structure.

Figure 1:
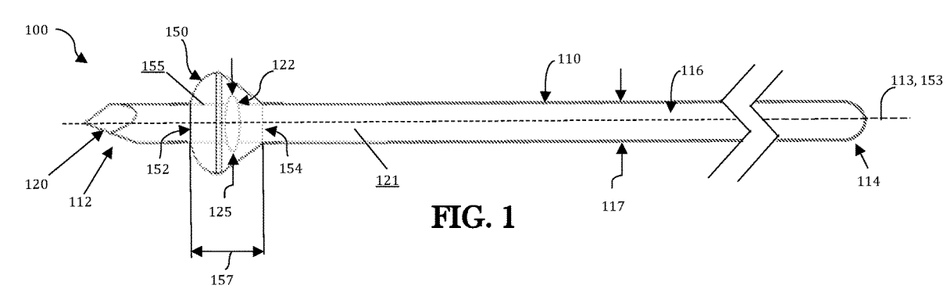
FIG. 1 illustrates a side view of an example bone fixation wire.

FIG. 1 illustrates an example bone fixation wire 100. The bone fixation wire comprises an elongate member 110 and a stopping member 150.

As illustrated in FIG. 1, the elongate member 110 has an elongate member first end 112, an elongate member second end 114, a lengthwise axis 113 extending between the elongate member first end 112 to the elongate member second end 114, a first outside diameter 117, an outer wall 116, and a retaining member 122. The elongate member first end 112 defines a tip 120 that extends from the elongate member first end 112 toward the elongate member second end 114. The outer wall 116 of the elongate member 110 defines an elongate member outer surface 121. The retaining member 122 is positioned on a portion of the outer wall 116 of the elongate member 110 between the elongate member first and second ends 112, 114. In the illustrated embodiment, the retaining member 122 extends circumferentially about the elongate member 110 and has a second outside diameter 125 that is greater than the first outside diameter. Thus, the retaining member 122 extends away from outer wall 116 and outer surface 121 of the elongate member 110. In the illustrated embodiment, the retaining member 122 extends perpendicularly from the lengthwise axis 113 of the elongate member 110.

In the illustrated embodiment, the elongate member 110 is a solid wire. It is noted, though, than a lumen-defining structure, such as a cannula, can also be used as the elongate member in a bone fixation wire according to a particular embodiment. Also, in the illustrated embodiment, the retaining member 122 is defined by the elongate member 110. It is noted, though, that a retaining member comprising a separate member that is secured to an appropriate elongate member can be used in a bone fixation wire according to a particular embodiment.

The tip 120 of the elongate member 110 may have any suitable size, shape, and structural configuration, and a skilled artisan will be able to select an appropriate configuration for a tip of an elongate member of a bone fixation wire according to an embodiment based on various considerations, including the nature of any particular tissue or bone material with which the bone fixation wire is intended to be used. Examples of suitable configurations include a trocar tip, a conical tip, a rounded tip, a blunt tip, a threaded tip, or any other structural configuration of a tip considered suitable for a particular application. In the illustrated embodiment, the tip 120 of the elongate member 110 is structurally configured as a trocar tip.

The retaining member 122 may have any suitable size, shape, and structural configuration, and a skilled artisan will be able to select an appropriate configuration for a retaining member according to an embodiment based on various considerations, including the size, shape, and configuration of a stopping member. Examples of suitable configurations include, but are not limited to, configurations having a cross-sectional shape that is circular, substantially circular, ovoid, elliptical, toroidal, rectangular, triangular, or any other cross-sectional shape considered suitable for a particular application. In the illustrated embodiment, the retaining member 122 includes a curvilinear shape that extends away from the elongate member 110 and is formed circumferentially about the lengthwise axis 113 of the elongate member 110, giving the retaining member 122 a circular cross-sectional shape relative to the lengthwise axis 113 of the elongate member 110.

While the retaining member 122 is disposed on a portion of the elongate member 110 that is closer to the elongate member first end 112 that it is to the elongate member second end, the retaining member 122 can be disposed along any suitable portion of an elongate member in a bone fixation wire according to a particular embodiment. A skilled artisan will be able to select a suitable position to dispose a retaining member to an elongate member according to a particular embodiment based on various considerations, including the type of medical device with which the stopping member interfaces and guides inside a body cavity. Example positions considered suitable for a retaining member to be positioned along an elongate member include, but are not limited to, a position between the elongate member first end and the medial portion of the elongate member, a position in the medial portion of the elongate member between the elongate member first and second ends, a position between the medial portion of the elongate member and the elongate member second end, and any other positions considered suitable for a particular application. In this illustrated embodiment, the retaining member 122 is positioned between the elongate member first end 112 and the geometric midpoint of the axial length of the elongate member 110 on the lengthwise axis 113 of the elongate member 110.

As illustrated in FIG. 1, the stopping member 150 has a stopping member first end 152, a stopping member second end 154, a lengthwise axis 153 that extends between the stopping member first end 152 and the stopping member second end 154, a stopping member outer surface 155, and a stopping member inner surface (not illustrated). As illustrated in this embodiment, the stopping member 150 is disposed on a portion of the elongate member 110 toward the elongate member first end 112 and extends along a partial length 157 of the elongate member 110 between the elongate member first end 112 and the elongate member second end 114. The stopping member first end 152 is positioned toward the elongate member first end 112, and the stopping member second end 154 is positioned toward the elongate member second end 114. The stopping member inner surface cooperatively engages the elongate member outer surface 121 and the retaining member 122 once the stopping member 150 is formed about the elongate member 110 by injection molding, which is described in detail below. The stopping member outer surface 155 may interface with a medical device during use of the bone fixation wire 100, such as an orthopedic bone plate, to guide the medical device to a desired location during placement, or the stopping member outer surface 155 may interface with a natural opening or artificially created bore in a patient's bone to limit the extent to which the elongate member 110 can extend into the opening or bore.

While the stopping member 150 is disposed on a portion of the elongate member 110 toward the elongate member first end 112 and extends along a length 157, the stopping member 150 can define any suitable length and be disposed on any suitable portion of an elongate member in a bone fixation wire according to a particular embodiment. A skilled artisan will be able to select a suitable position to attach the stopping member to an elongate member according to a particular embodiment based on various considerations, including the type of medical device with which the stopping member interfaces and guides inside a body cavity. Example positions considered suitable for a stopping member to be positioned along an elongate member include a position between the elongate member first end and the medial portion of the elongate member, a position in the medial portion of the elongate member between the elongate member first and second ends, a position between the medial portion of the elongate member and the elongate member second end, and any other positions considered suitable for a particular application. In this illustrated embodiment, the stopping member 150 is positioned toward the elongate member first end 112 between the elongate member first end 112 and the geometric midpoint of the axial length of the elongate member 110 on the lengthwise axis 113 of the elongate member 110.

As best illustrated in FIG. 1, the stopping member 150 in the illustrated embodiment is configured as a beadlike shape in which the stopping member first end 152 increases in diameter toward a medial portion of the stopping member 150 and then linearly decreases in diameter from the medial portion toward the stopping member second end 154. While the stopping member 150 defines a beadlike shape configuration, the stopping member may have any suitable size, shape, and configuration parameters, and a skilled artisan will be able to select an appropriate configuration for a stopping member in a bone fixation wire according to a particular embodiment based on various considerations, including the nature of any particular medical device with which the stopping member is intended to interface with or guide during use. Example structural configurations suitable for a stopping member include toridal, tubular, circular, substantially circular, elliptical, ovoid, and any other suitable structural configuration.

As illustrated in FIG. 1, the stopping member 150 is circumferentially formed about a portion of the elongate member 110 and about the retaining member 122, which is discussed in detail below. Forming the stopping member 150 over a portion of the elongate member 110 and the retaining member 122 is considered advantageous at least because the retaining member 122 prevents any axial or rotational movement between the stopping member 150 and the elongate member 110 during use. Thus, the retaining member 122 holds the stopping member 150 to a fixed position while a user, such as a surgeon, inserts the bone fixation wire 100 into a patient or withdraws the bone fixation wire 100 from a patient for orthopedic uses.

Figure 2:
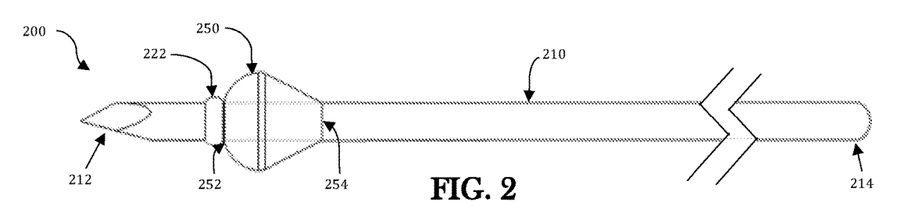
FIG. 2 illustrates a side view of another example bone fixation wire.

FIG. 2 illustrates another example bone fixation wire 200 that includes a stopping member 250 attached to an elongate member 210, and the elongate member 210 defines a retaining member 222. The bone fixation wire 200 is similar to the bone fixation wire 100 described above, except as detailed below. In this illustrated embodiment, the stopping member 250 is circumferentially formed about the elongate member 210 and abuts the retaining member 222. As best illustrated in FIG. 2, the retaining member 222 is defined toward the elongate member first end 212 and interfaces with the stopping member first end 252 to prevent axial or rotational movement. To prevent any axial or rotational movement between the elongate member 210 and the stopping member second end 254, an adhesive can be applied between these two elements or a friction fit cab be utilized.

Figure 3:
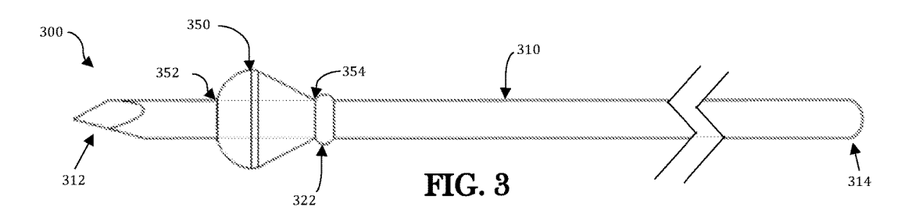
FIG. 3 illustrates a side view of another example bone fixation wire.

FIG. 3 illustrates another example bone fixation wire 300 that includes a stopping member 350 attached to an elongate member 310, and the elongate member 310 defines a retaining member 322. The bone fixation wire 300 is similar to the bone fixation wire 100 described above, except as detailed below. In the illustrated embodiment, the stopping member 350 is circumferentially formed about the elongate member 310 and abuts the retaining member 322. As best illustrated in FIG. 3, the retaining member 322 is defined toward the medial portion of the elongate member 310 and interfaces with the stopping member second end 354 to prevent axial or rotational movement. To prevent any axial or rotational movement between the elongate member 310 and the stopping member first end 352, an adhesive can be applied between these two elements or a friction fit cab be utilized.

Figure 4:
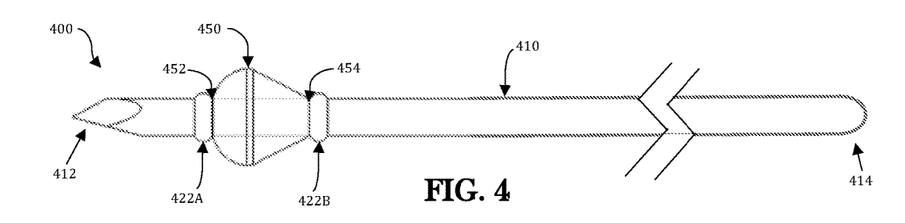
FIG. 4 illustrates a side view of another example bone fixation wire.

FIG. 4 illustrates another example bone fixation wire 400 that includes a stopping member 450 circumferentially formed about the elongate member 410. The bone fixation wire 400 is similar to the bone fixation wire 100 described above, except as detailed below. In the illustrated embodiment, the elongate member 410 includes a first retaining member 422A and a second retaining member 422B, and the stopping member 450 is disposed between a first retaining member 422A and a second retaining member 422B. As best illustrated in FIG. 4, the first retaining member 422A is defined toward the elongate member first end 412, and the second retaining member 422B is defined toward the elongate member second end 414. The positions of the first and second retaining members 422A, 422B are considered advantageous at least because each of the first and second retaining members 422A, 422B restricts axial or rotational movement of the stopping member 450 while the bone fixation wire 400 is inserted into a body cavity or withdrawn from a body cavity during use.

Each of the retaining members 422A, 422B can have any suitable size, shape, and structural configuration, and a skilled artisan will be able to select an appropriate configuration for a retaining member according to an embodiment based on various considerations, including the size, shape, and configuration of a stopping member. Examples of suitable configurations include, but are not limited to, configurations having a cross-sectional shape that is circular, substantially circular, ovoid, elliptical, toroidal, rectangular, triangular, or any other cross-sectional shape considered suitable for a particular application. In the illustrated embodiment, the each of the retaining members 422A, 422B includes a curvilinear shape that extends away from the elongate member 410 and is formed circumferentially about the lengthwise axis 413 of the elongate member 410, giving each of the retaining members 422A, 422B a circular cross-sectional shape relative to the lengthwise axis of the elongate member 410. Additionally, the elongate member 410 may have any suitable number of retaining members, and a skilled artisan will be able to select an appropriate number of retaining members according to an embodiment based on various considerations, including the size, shape and configuration of a stopping member. Examples of suitable numbers of retaining members disposed on an elongate member include one, two, more than two, at least two, a plurality, three, four, five, six, or any other number of retaining members for considered suitable for a particular application. In the illustrated embodiment, the elongate member 410 includes two retaining members 422A, 422B.

Figure 5:
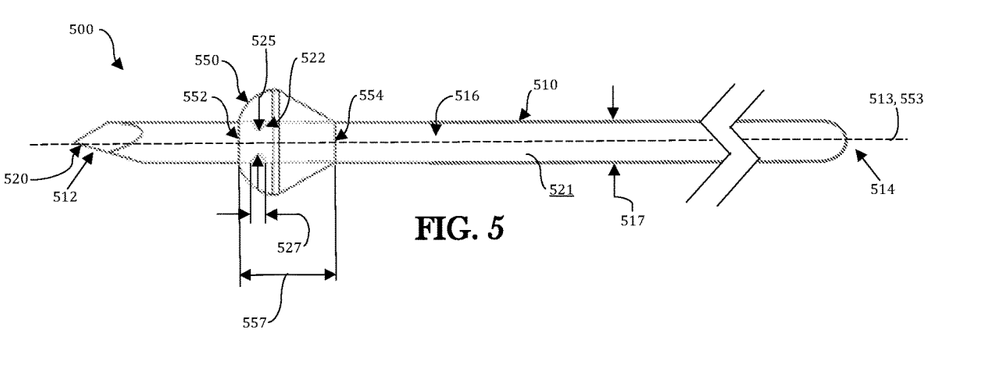
FIG. 5 illustrates a side view of another example bone fixation wire.

FIG. 5 illustrates another example bone fixation wire 500. The bone fixation wire 500 includes an elongate member 510 and a stopping member 550. The bone fixation wire 500 is similar to the bone fixation wire 100 described above, except as detailed below. The elongate member 510 has an elongate member first end 512, an elongate member second end 514, a lengthwise axis 513 extending between the elongate member first end 512 to the elongate member second end 514, a first outside diameter 517, and an outer wall 516 defining an elongate member outer surface 521.

In this embodiment, the elongate member outer surface 521 defines a circumferential groove 522 having a second outside diameter 525 and an axial length 527. The circumferential groove 522 is disposed on a portion of the outer wall 516 of the elongate member 510 between the elongate member first end 512 and the elongate member second end 514. In the illustrated embodiment, the circumferential groove 522 extends into the elongate member 510 perpendicularly toward the lengthwise axis 513 of the elongate member 510. The second outside diameter 525 of the circumferential groove 522 is less than the first outside diameter 517 of the elongate member 110.

The circumferential groove 522 may have any suitable size, shape, and structural configuration, and a skilled artisan will be able to select an appropriate configuration for a circumferential groove for use in a bone fixation wire according to a particular embodiment based on various considerations, including the size, shape, and configuration of the stopping member used in the bone fixation wire. Examples of suitable configurations include, but are not limited to, configurations having a cross-sectional shape that is semi-circular, substantially semi-circular, semi-ovoid, semi-elliptical, rectangular, triangular, or any other cross-sectional shape considered suitable for a particular application. In the illustrated embodiment, the circumferential groove 522 includes a curvilinear shape that extends into the elongate member 510 and is formed circumferentially about the lengthwise axis 513 of the elongate member 510, giving the circumferential groove 522 a semi-circular cross-sectional shape relative to the lengthwise axis 513 of the elongate member 510.

While the circumferential groove 522 is disposed on a portion of the elongate member 510 toward the elongate member first end 512, a retaining member can be disposed along any suitable portion of an elongate member. A skilled artisan will be able to select a suitable position to dispose a retaining member to an elongate member according to a particular embodiment based on various considerations, including the type of medical device with which the stopping member interfaces and guides inside a body cavity. Example positions considered suitable for a retaining member to be positioned along an elongate member include a position between the elongate member first end and the medial portion of the elongate member, a position in the medial portion of the elongate member between the elongate member first and second ends, a position between the medial portion of the elongate member and the elongate member second end, and any other positions considered suitable for a particular application. In this illustrated embodiment, the circumferential groove 522 is positioned toward the elongate member first end 512 between the elongate member first end 512 and the medial portion of the elongate member 510.

As illustrated in FIG. 5, the stopping member 550 has a stopping member first end 552, a stopping member second end 554, a lengthwise axis 553 that extends between the stopping member first end 552 and the stopping member second end 554, a stopping member outer surface 555, and a stopping member inner surface (not illustrated). As illustrated in the embodiment, the stopping member 550 is disposed on a portion of the elongate member 510 toward the elongate member first end 512 and extends between the elongate member first and second ends 512, 514 that defines a length 557. The stopping member first end 552 is positioned toward the elongate member first end 512, and the stopping member second end 554 is positioned toward the elongate member second end 514. The stopping member inner surface cooperatively engages the elongate member outer surface 521 and the circumferential groove 522 once the stopping member 550 is formed about the elongate member 510 during injection molding, which is described in detail below. The stopping member outer surface 555 may interface with a medical device during use of the bone fixation wire 500, such as an orthopedic bone plate, to guide the medical device to a desired location during placement, or the stopping member outer surface 555 may interface with a natural opening or artificially created bore in a patient's bone to limit the extent to which the elongate member 510 can extend into the opening or bore.

As illustrated in FIG. 5, the stopping member 550 is circumferentially formed about a portion of the elongate member 510 and is extends into the circumferential groove 522, which is discussed in detail below. Forming the stopping member 550 about a portion of the elongate member 510 such that it extends into the circumferential groove 522 is considered advantageous at least because the circumferential groove 522 of the elongate member 510 prevents any axial or rotational movement between the stopping member 550 and the elongate member 510 during use. Thus, the circumferential groove 522 holds the stopping member 550 to a fixed position while a user, such as a surgeon, inserts the bone fixation wire 500 into a bore in a bone or withdraws the bone fixation wire 500 from such a bore for orthopedic uses.

Figure 6:
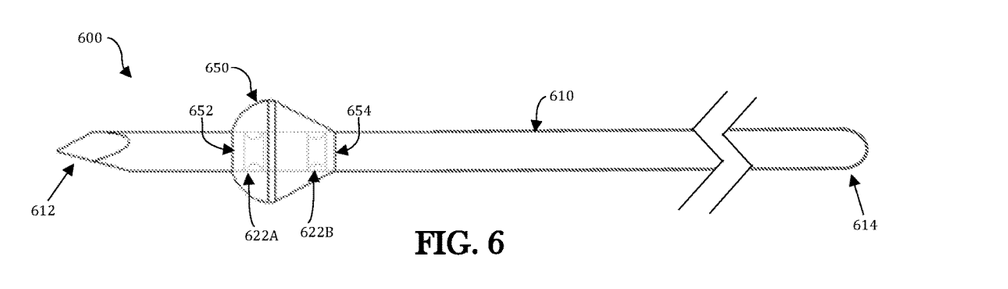
FIG. 6 illustrates a side view of another example bone fixation wire.

FIG. 6 illustrates another bone fixation wire 600 that includes a stopping member 650 circumferentially formed about the elongate member 610. The bone fixation wire 600 is similar to the bone fixation wire 500 described above, except as detailed below. In this example, the elongate member 610 includes a first circumferential groove 622A and a second circumferential groove 622B, and a portion of the stopping member 650 extends into each of the first and second circumferential grooves 622A, 622B. As best illustrated in FIG. 6, the first circumferential groove 622A is defined toward the elongate member first end 612, and the second circumferential groove 622B is defined toward the elongate member second end 614. These positions of the first and second circumferential grooves 622A, 622B are considered advantageous at least because each of the first and second circumferential grooves 622A, 622B restricts axial or rotational movement of the stopping member 650 while the bone fixation wire 600 is inserted into a body cavity or withdrawn from a body cavity during use.

Each circumferential groove 622A, 622B may have any suitable size, shape, and structural configuration, and a skilled artisan will be able to select an appropriate configuration for a circumferential groove for use in a bone fixation wire according to a particular embodiment based on various considerations, including the size, shape, and configuration of the stopping member used in the bone fixation wire. Examples of suitable configurations include, but are not limited to, configurations having a cross-sectional shape that is semi-circular, substantially semi-circular, semi-ovoid, semi-elliptical, rectangular, triangular, or any other cross-sectional shape considered suitable for a particular application. In the illustrated embodiment, each circumferential groove 622A, 622B includes a curvilinear shape that extends into the elongate member 610 and is formed circumferentially about the lengthwise axis 613 of the elongate member 610, giving each circumferential groove 622A, 622B a semi-circular cross-sectional shape relative to the lengthwise axis of the elongate member 610. Additionally, the elongate member 610 in a bone fixation wire according to a particular embodiment may have any suitable number of circumferential grooves, and a skilled artisan will be able to select an appropriate number of circumferential grooves based on various considerations, including the size, shape and configuration of a stopping member in the bone fixation wire. Examples of suitable numbers of circumferential grooves disposed on an elongate member include one, two, more than two, at least two, a plurality, three, four, five, six, or any other number considered suitable for a particular application. In the illustrated embodiment, the elongate member 610 includes two circumferential grooves 622A, 622B.

Figure 7:
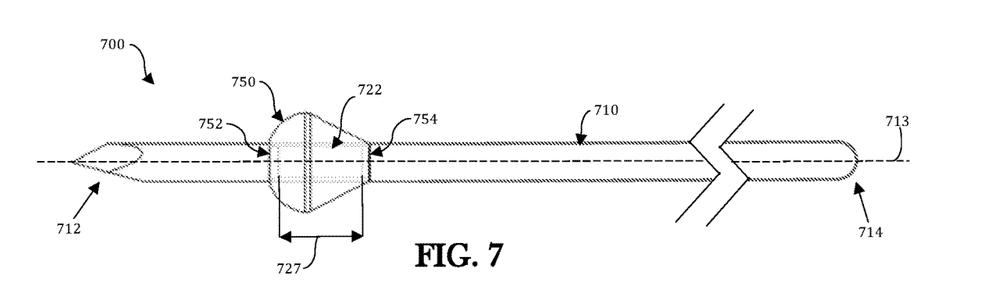
FIG. 7 illustrates a side view of another example bone fixation wire.

FIG. 7 illustrates another bone fixation wire 700 that includes a stopping member 750 circumferentially formed about the elongate member 710. The bone fixation wire 700 is similar to the bone fixation wire 500 described above, except as detailed below. In this example, the elongate member 710 defines a notch 722 that extends into the elongate member 710 relative to the lengthwise axis of the elongate member. In the illustrated embodiment, the notch 722 defines an axial length 727 that extends along an axial portion of the elongate member 710 between the elongate member first end 712 and the elongate member second end 714. The stopping member 750 is formed about the elongate member such that a portion of the stopping member 750 extends into the notch 722, which prevents any axial or rotational movement between the stopping member 750 and the elongate member 710 during use. Thus, the retaining member 722 holds the stopping member 750 to a fixed position while a user, such as a surgeon, inserts the bone fixation wire 700 into a bore in a bone or withdraws the bone fixation wire 700 from such a bore for orthopedic uses.

The notch 722 may have any suitable size, shape, and structural configuration, and a skilled artisan will be able to select an appropriate configuration for a notch for use in a bone fixation wire according to a particular embodiment based on various considerations, including the size, shape, and configuration of the stopping member used in the bone fixation wire. Examples of suitable configurations include, but are not limited to, configurations having a cross-sectional shape that is semi-circular, substantially semi-circular, semi-ovoid, semi-elliptical, rectangular, triangular, or any other cross-sectional shape considered suitable for a particular application. In the illustrated embodiment, the notch 722 includes a rectangular shape that extends into the elongate member 710, giving the notch 722 a rectangular cross-sectional shape relative to the lengthwise axis of the elongate member 710.

Figure 8:
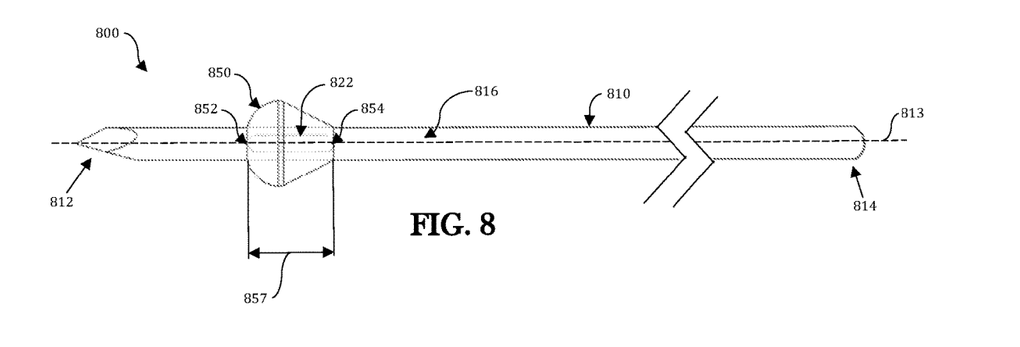
FIG. 8 illustrates a side view of another example bone fixation wire.

FIG. 8 illustrates another example bone fixation wire 800. The bone fixation wire 800 is similar to the bone fixation wire 100 described above, except as detailed below. The bone fixation wire 800 includes an elongate member 810 and a stopping member 850. In this example, the elongate member 810 has an elongate member first end 812, an elongate member second end 814, a lengthwise axis 813 extending between the elongate member first end 812 to the elongate member second end 814, an outer wall 816 defining an elongate member outer surface 821, and a passageway 822 that extends completely through the elongate member 810, from one side of the elongate member 810 to another side relative to the lengthwise axis 813 of the elongate member 810.

In the illustrated embodiment, the passageway 822 defines a retaining member axial length 857 that extends along an axial portion of the elongate member 810 between the elongate member first end 812 and the elongate member second end 814. The passageway 822 is positioned on a portion of the outer wall 816 of the elongate member 810 between the elongate member first end and the elongate member second end 814 near the elongate member first end 812. The passageway 822 extends into the outer wall 816 of the elongate member 810 and through the entire thickness of the material of the elongate member 810.

The passageway 822 may have any suitable size, shape, and structural configuration, and a skilled artisan will be able to select an appropriate configuration for a passageway for use in a bone fixation wire according to a particular embodiment based on various considerations, including the size, shape, and configuration of the stopping member used in the bone fixation wire. Examples of suitable configurations include, but are not limited to, configurations having a cross-sectional shape that is circular, substantially circular, ovoid, elliptical, rectangular, triangular, or any other cross-sectional shape considered suitable for a particular application. In the illustrated embodiment, the passageway 822 includes an elliptical shape that extends into and through the elongate member 810, giving the passageway 822 an elliptical cross-sectional shape relative to the lengthwise axis of the elongate member 810.

While the passageway 822 is disposed on a portion of the elongate member 810 toward the elongate member first end 812, the passageway 822 can extend along any suitable axial portion of an elongate member 810. A skilled artisan will be able to select a suitable position for a passageway on an elongate member in a bone fixation wire according to a particular embodiment based on various considerations, including the size, shape, and configuration of the stopping member used in the bone fixation wire. Example positions considered suitable for a passageway include a position between the elongate member first end and the geometric midpoint of the axial length of the elongate member, a position in which the passageway extends across the geometric midpoint of the axial length of the elongate member, a position between the geometric midpoint of the axial length of the elongate member and the elongate member second end, and any other position considered suitable for a particular application. In this illustrated embodiment, the passageway 822 is positioned between the elongate member first end 812 and the geometric midpoint of the axial length of the elongate member 810 on the lengthwise axis 813 of the elongate member 810. The passageway 822 has an axial length that extends along a partial length of the elongate member 810 between the elongate member first end 812 and the elongate member second end 814, and has a width that extends perpendicular to the lengthwise axis 813 of the elongate member 813. In this embodiment, the axial length of the passageway 822 is greater than the axial width of the passageway 822.

As illustrated in FIG. 8, the stopping member 850 has a stopping member first end 852, a stopping member second end 854, a lengthwise axis 853 that extends between the stopping member first end 852 and the stopping member second end 854, a stopping member outer surface 855, and a stopping member inner surface (not illustrated). In this embodiment, the stopping member 850 is disposed on a portion of the elongate member 810 toward the elongate member first end 812 and extends along a partial length 857 of the elongate member 810 between the elongate member first end 812 and the elongate member second end 814. The stopping member first end 852 is positioned toward the elongate member first end 812, and the stopping member second end 854 is positioned toward the elongate member second end 814. The stopping member inner surface cooperatively engages the elongate member outer surface 821 and the passageway 822 once the stopping member 850 is formed about the elongate member 810 during injection molding, which is described in detail below. The stopping member outer surface 855 may interface with a medical device during use of the bone fixation wire 800, such as an orthopedic bone plate, to guide the medical device to a desired location during placement, or the stopping member outer surface 855 may interface with a natural opening or artificially created bore in a patient's bone to limit the extent to which the elongate member 810 can extend into the opening or bore.

Figure 9:
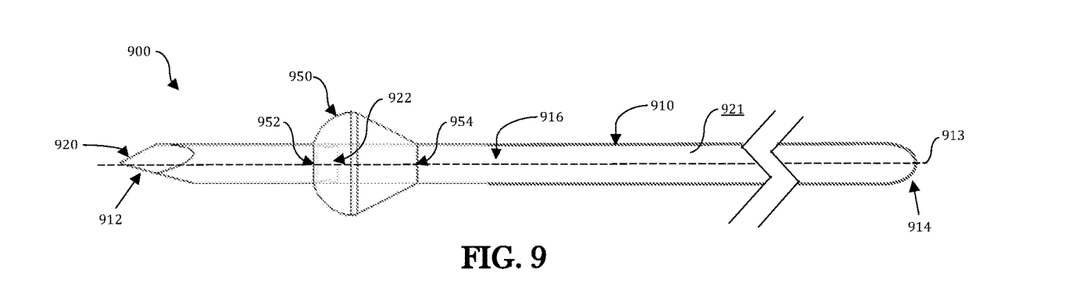
FIG. 9 illustrates a side view of another example bone fixation wire.

FIG. 9 illustrates another example bone fixation wire 900 that includes a stopping member 950 circumferentially formed about the elongate member 910. The bone fixation wire 900 is similar to the bone fixation wire 800 described above, except as detailed below. The elongate member 910 defines a passageway 922 that extends from one side of the elongate member 910 to the other side of the elongate member 910. The passageway 922 is positioned between the elongate member first end 912 and the elongate member second end 914 near the elongate member first end 912. The passageway 922 extends entirely through the elongate member 910 relative to the lengthwise axis 913 of the elongate member 910. The stopping member 950 is formed about the elongate member 910 and extends into and through the passageway 922 such that a portion of the stopping member is disposed within the passageway 922 of the elongate member 910. The passageway 922 has an axial length that extends along a partial length of the elongate member 910 between the elongate member first end 912 and the elongate member second end 914, and has a width that extends perpendicular to the lengthwise axis 913 of the elongate member 913. In this embodiment, the axial width of the passageway 922 is greater than the axial length of the passageway 922.

Figure 10:
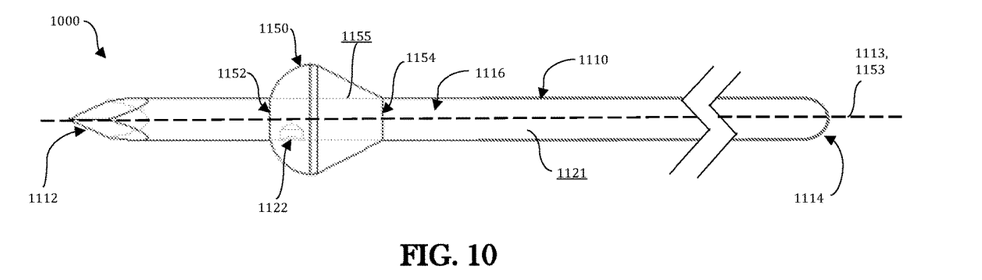
FIG. 10 illustrates a side view of another example bone fixation wire.

FIG. 10 illustrates another example bone fixation wire 1000. The bone fixation wire 1000 in this embodiment is similar to the bone fixation wire 100 illustrated in FIG. 1 and described above, except as detailed below. The bone fixation wire 1000 includes an elongate member 1110 and a stopping member 1150. In this example, the elongate member 1100 has an elongate member first end 1112, an elongate member second end 1114, a lengthwise axis 1113 extending between the elongate member first end 1112 to the elongate member second end 1114, an outer wall 1116 that defines an elongate member outer surface 1121, and a depression formed in the outer wall.

In the illustrated embodiment, the depression is positioned on a portion of the outer wall 1116 of the elongate member 1100 between the elongate member first end 1112 and the elongate member second end 1114 near the elongate member first end 1112. In this embodiment, the protrusion 1122 comprises a portion of the stopping member 1150 that is formed such that it extends into the depression defined by the outer wall 1116 of the elongate member 1100 by a mold during an injection molding process, such as the method described in detail below. The mold includes a puncturing member that creates the depression once the mold is placed on the elongate member 1100 during injection molding. Subsequently, the protrusion 1122 is formed when the stopping member 1150 is formed about the elongate member such that the protrusion 1122 extends into the depression in the outer wall 1116 of the elongate member 1110.

The stopping member 1150 has a stopping member first end 1152, a stopping member second end 1154, a lengthwise axis 1153 that extends between the stopping member first end 1152 and the stopping member second end 1154, a stopping member outer surface 1155, and a stopping member inner surface. The stopping member 1150 is disposed on a portion of the elongate member 1110 toward the elongate member first end 1112 and extends along an axial portion 1157 of the elongate member 1110 between the elongate member first end 1112 and the elongate member second end 1114. The stopping member first end 1152 is positioned toward the elongate member first end 1112, and the stopping member second end 1154 is positioned toward the elongate member second end 1114. The stopping member inner surface cooperatively engages the elongate member outer surface 1121 and the protrusion 1122 extends into the depression once the stopping member 1150 is formed about the elongate member 1110. The stopping member outer surface 1155 may interface with a medical device during use of the bone fixation wire 1000, such as an orthopedic bone plate, to guide the medical device to a desired location during placement, or the stopping member outer surface 1155 may interface with a natural opening or artificially created bore in a patient's bone to limit the extent to which the elongate member 1110 can extend into the opening or bore.

In this embodiment, the puncturing member of the mold is configured to be retractable. Before the first mold is introduced to the elongate member 1110, the puncturing member is housed inside of the first mold through use of a passageway or a cavity defined by the first mold. The puncturing member is introduced into the elongate member 1110 by means of an actuation member that enables the puncturing member to transition from a first position to a second position. The actuation member of the first mold defines a mechanical feature that is attached to the puncturing member to allow retraction of the puncturing member. Once the mechanical feature of the actuation member is activated from a first state to second state, the puncturing member is enabled to transition from a first position to a second position to which the puncturing member extends away from the first mold to form the depression in the elongate member 1100. Once the puncturing member creates the depression in the elongate member 1100, the puncturing member can be retracted into the first mold. The puncturing member is retracted from the second position to the first position by activating the mechanical feature of the actuation member from the second state to the first state. Once retracted, the puncturing member is housed inside the first mold before molten material is injected into the first mold to form the stopping member 1150 such that the protrusion is formed and extends into the depression. This structural configuration of retracting the puncturing member is considered advantageous at least because the formation of the stopping member 1150 can be performed quicker and more accurately by introducing only a single mold onto the elongate member 1100 rather than introducing at least two different molds onto the elongate member 1100.

The mechanical feature of the actuation member described in the present application to activate the puncturing member from a first position to a second position can have any suitable structural configuration. Skilled artisans will be able to determine a suitable mechanical feature for the activation member that can retract the puncturing member during use. Examples of suitable mechanical features include, but are not limited, a spring mechanism, a locking or unlocking mechanism, and any other suitable mechanical features for a particular application.

The puncturing member described in the present application may have any suitable size, shape, and structural configuration, and a skilled artisan will be able to select an appropriate configuration for a puncturing member to penetrate an elongate member of a bone fixation wire according to an embodiment based on various considerations, including the nature of any particular materials with which the puncturing member is intended to penetrate. Examples of suitable configurations include, but are not limited to, a trocar tip, a conical tip, a threaded tip, or any suitable structural configuration of a puncturing member for a particular application.

Figure 11:
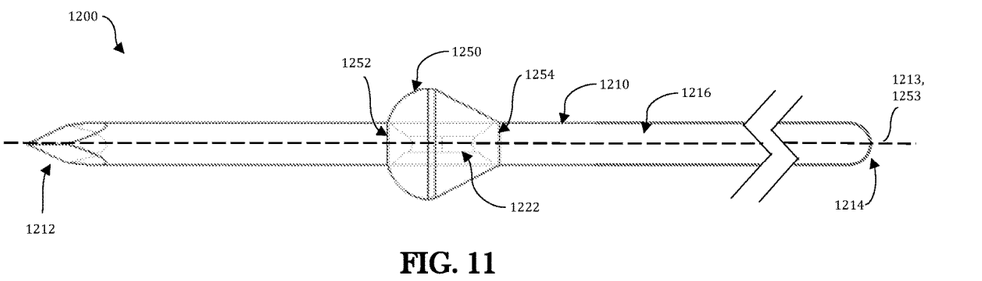
FIG. 11 illustrates a side view of another example bone fixation wire.
Figure 12:
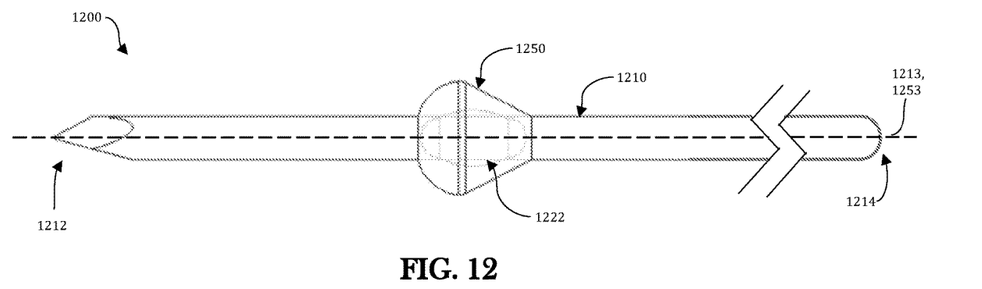
FIG. 12 illustrates a top view of the bone fixation wire illustrated in FIG. 11.

Each of the FIGS. 11 and 12 illustrates another bone fixation wire 1200 that includes a stopping member 1250 circumferentially formed about the elongate member 1210 by injection molding. The elongate member 1210 includes a flattened portion 1222 that is positioned on a portion of the outer wall 1216 of the elongate member 1210 between the elongate member first and second ends 1212, 1214 near the axially medial portion of the elongate member 1210. In this embodiment, a portion of the stopping member 1250 is formed such that it extends into the flattened portion 1222 defined by the outer wall 1216 of the elongate member 1200 by a mold during an injection molding process, such as the method described in detail below. Before the stopping member 1250 is formed about the elongate member 1210, the mold creates the flattened portion 1222 on the elongate member 1210 such that a portion of the stopping member 1250 extends into the flattened portion 1222 of the elongate member 1210. Once the mold forms the flattened portion 1222 on the elongate member 1210, a molten material is injected into the mold to form the stopping member 1250 about the elongate member 1210 such that a portion of the stopping member extends into the flattened portion 1222.

The elongate member in a bone fixation wire according to an embodiment can be made from any material suitable for use in medical devices intended for orthopedic use, including materials suitable for use in procedural tools and materials suitable for use in long-term implants. Examples of suitable materials for use in elongate members in bone fixation wires according to embodiments include metals, metal alloys, and polymeric materials, including plastics. Examples of suitable metals include, but are not limited to, Titanium, Magnesium, and other metals. Examples of suitable metal alloys include, but are not limited to, stainless steel, Ti6Al4V, 316 LVM, 1.4441Ti-13Nb-13Zr, Ti-12Mo-6Zr-2Fe, Ti-15Mo-5Zr-3Al, Ti15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamid, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamid CFR, and PA66 CFR.

The stopping member in a bone fixation wire according to an embodiment can be made from any material suitable for use in medical devices intended for orthopedic use, including materials suitable for use in procedural tools and materials suitable for use in long-term implants. Examples of suitable materials for use in stopping members in bone fixation wires according to embodiments include metals, metal alloys, and polymeric materials, including plastics. Examples of suitable metals include, but are not limited to, Titanium, Magnesium, and other metals. Examples of suitable metal alloys include, but are not limited to, Ti6Al4V, 316 LVM, 1.4441Ti-13Nb-13Zr, Ti-12Mo-6Zr-2Fe, Ti-15Mo-5Zr-3Al, Ti15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamid, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamid CFR, and PA66 CFR.

The inventors have determined that bone fixation wires in which the elongate member comprises a metal or a metal alloy and in which the stopping member comprises a polymeric material, such as a plastic, are particularly advantageous at least because the contrast in various physical characteristics of the different types of material, including density, thermal conductivity, and tactile properties. For example, the inventors believe a bone fixation wire including an elongate member comprising a metal or metal alloy provide desirable balance and handling properties during use. Existing bone fixation wires comprising a monolithic metal structure are often cold during use and provide an undesirable degree of tactile feedback during use, which can ultimately impact the placement and securement of a medical device, such as a bone plate. Furthermore, the use of these different materials in the elongate member and stopping member components of a bone fixation wire allow for the use of more efficient methods of making, including overmolding the elongate member with the stopping member, such as in the example method of making described below.

Figure 13:
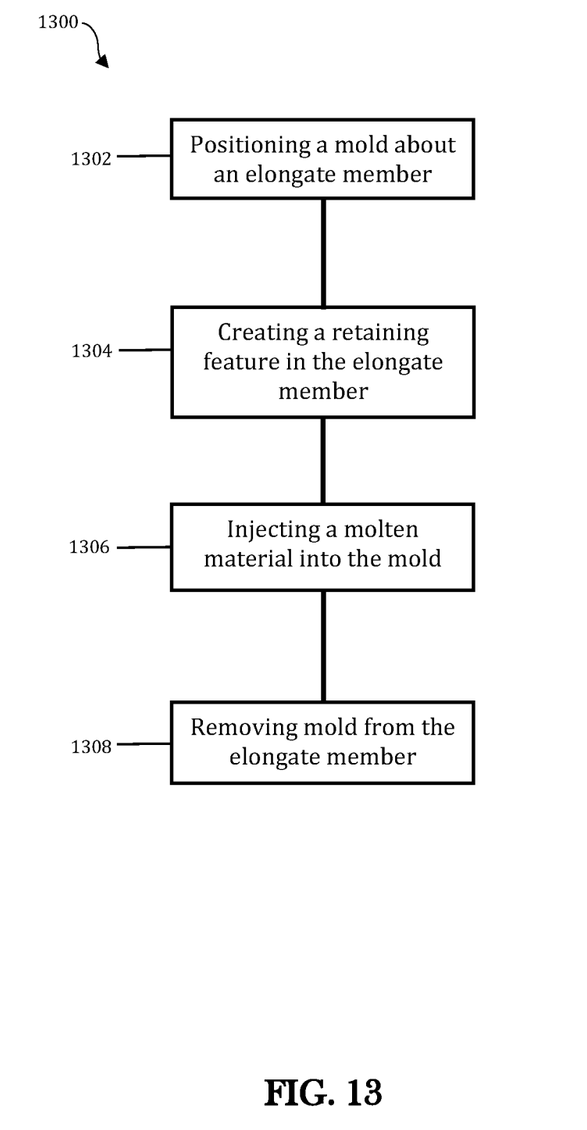
FIG. 13 illustrates a flowchart representation a method of making a bone fixation wire.

FIG. 13 illustrates a flowchart representation of a method 1300 of making a bone fixation wire. Performance of the method 1300 produces a bone fixation wire according to an embodiment of the invention, such as one or more of the example bone fixation wires described and illustrated herein. With this method, it is expected that the making of the inventive bone fixation wire will require less of relatively expensive materials, including metals, while producing suitable structural arrangements between the stopping member and the elongate member to provide a bone fixation wire having desirable properties.

The use of injection molding to form the stopping member on the elongate member is considered advantageous at least because the process allows for a structural attachment between the stopping member and the retaining member. For example, injection molding can be used to form a stopping member on an elongate member such that the stopping member is disposed about a retaining member formed by or disposed on the elongate member, such that the stopping member is abuts one or more retaining members formed by or disposed on the elongate member, such that the stopping member is disposed between a first and second retaining member formed by or disposed on the elongate member, or such that the stopping member includes a protrusion that extends into a retaining feature formed by the elongate member, such as a circumferential groove, depression, or other structural feature of the elongate member. Additionally, forming the stopping member onto the elongate member by injection molding increases the flexibility of the stopping member in comparison to traditional bone fixation wires. The flexibility of the stopping member may allow a user, such as a surgeon, to manipulate or bend the bone fixation wire more adequately than a traditional bone fixation wire during implantation. Injection molding also allows the stopping member to be formed in a variety of shapes and configurations, including shapes and configurations customized for particular uses and/or requests from users. Furthermore, molding the stopping member onto the elongate member by use of injection molding allows for a larger difference in the diameters of the elongate member and the stopping member as compared to the difference in diameters in conventional bone fixation wires, which is generally limited because increasing the difference between the diameters of these localized portions of conventional monolithic metal bone fixation wires increases the amount of wasted material in the manufacture of such wires, which usually involves machining the final monolithic wire from initial rod stock.

An initial step 1302 comprises placing a mold, as described above, circumferentially about an elongate member. The mold can be placed at any suitable position along the elongate member. In some methods, the elongate member comprises a solid rod; in other methods, the elongate member comprises a cannula defining a lumen.

An optional step 1304 comprises creating a retaining feature in the elongate member. This step can be accomplished, if included, by actuating an appropriate mechanical feature of the mold that results in a puncturing member of the mold moving from a first position to a second position to create the retaining feature in the elongate member. In one example, once the mold is properly set on the elongate member, the puncturing member transitions from a first position to a second position by activating the actuation member. Once the actuation member is actuated, the puncturing member penetrates the circumferential wall of the elongate member such that the puncturing member extends into the elongate member perpendicularly to the lengthwise axis of the elongate member. When the elongate member comprises a cannula, the puncturing member can extend through the outer wall to create an opening into the lumen of the elongate member. Once the puncturing member creates the retaining feature in the elongate member, the puncturing member can be retracted into the mold by actuating the actuation member from the second state to the first state. Once retracted, the puncturing member is again inside the mold before molten material is injected into the first mold to form the stopping member.

When the elongate member comprises a rod, the mold can include a flattening member. In these methods, once the second mold is properly set on the elongate member, the flattening member engages the outer wall of the elongate member such that the flattening member compresses one or two sides of the elongate member perpendicularly to the lengthwise axis of the elongate member. The flattening member compresses a portion of the outer wall of the elongate member to a reduced diameter, creating a flattened portion on the elongate member.

An optional step comprises making an elongate member that defines a retaining member prior to positioning a mold on the elongate member. This optional step should be performed prior to step 1302 and 1304, if included, and should be performed such that an elongate member suitable for use in a bone fixation wire according to an embodiment is produced.

Another step 1306 comprises injecting a molten material into the mold to create a stopping member on the elongate member, such as bone fixation wire 1000 in FIG. 10. This step can be accomplished by using any suitable technique, include any suitable injection molding technique and any suitable injection tool, such as a syringe. Once the molten material is injected into the mold, the material will form inside the mold to create a predetermined shape for a stopping member, including any relevant protrusion that extends into a structural retaining feature define by the elongate member, if appropriate.

An optional step comprises applying additional materials to the elongate member and/or the stopping member. This optional step, if included, can be performed to enhance the mechanical attachment of the stopping member to the elongate member. This step can be accomplished prior to the step 1306 of injecting a molten material into the mold by applying any suitable material, such as an adhesive or binder, to a specific portion of the elongate member outer surface where the stopping member is to be formed. Alternatively, this step can be accomplished during or subsequent to performance of the step 1306 of injecting a molten material into the mold. For example, this step can comprises applying an adhesive material to the elongate member where the elongate member contacts the stopping member formed by performance of the step 1306 of injecting a molten material into the mold. This optional step is considered advantageous at least because the adhesive material restricts axial or rotational movement where a portion of the stopping member does not interface or is not bonded to a retaining member defined by the elongate member.

Another step 1308 comprises removing the mold from the elongate member. This step is accomplished once the stopping member is formed and attached to the elongate member outer surface. This step can be accomplished by using any suitable technique and/or tools.

Another optional step comprises creating an additional mechanical attachment between the elongate member and the stopping member. This step can be accomplished after subsequent to performance of the step 1308 of removing the mold, for example, by crimping a portion of the stopping member to a portion of the elongate member. This optional step is considered advantageous at least because the mechanical attachment restricts axial or rotational movement where a portion of the stopping member does not interface or is not bonded to a retaining member defined by elongate member.

The foregoing detailed description provides example embodiments of the invention and includes the best mode for practicing the invention. The description and illustration of embodiments is intended only to provide examples of the invention and not to limit the scope of the invention, or its protection, in any manner.

We claim:

1. A bone fixation wire, comprising:
an elongate member having an elongate member first end defining a tip, an elongate member second end, and a lengthwise axis extending between the elongate member first end and the elongate member second end, the elongate member defining an outer wall extending between the elongate member first end and the elongate member second end;
a first retaining member disposed on the elongate member outer wall between the elongate member first end and the geometric midpoint of the axial length of the elongate member on the lengthwise axis, the retaining member defining a first outer diameter; and
a stopping member disposed on the elongate member and contacting the retaining member, the stopping member having a stopping member first end, a stopping member second end, a stopping member outer surface, and a stopping member inner surface, the stopping member inner surface contacting the elongate member outer surface and defining a stopping member inner lumen having an inner diameter;
wherein the elongate member comprises a first material; and
wherein the stopping member comprises a second material that is different from the first material.

2. The bone fixation wire of claim 1, wherein the stopping member is disposed over the first retaining member.

3. The bone fixation wire of claim 1, wherein the first outer diameter is greater than the inner diameter.

4. The bone fixation wire of claim 3, wherein the stopping member first end contacts the first retaining member.

5. The bone fixation wire of claim 4, further comprising a second retaining member disposed on the elongate member outer wall between the elongate member second end and the first retaining member; the second retaining member defining a second outer diameter;
wherein the second outer diameter is greater than the inner diameter; and
wherein the stopping member is disposed between the first and second retaining members on the lengthwise axis of the elongate member.

6. The bone fixation wire of claim 5, wherein the stopping member second end contacts the second retaining member.

7. The bone fixation wire of claim 1, wherein the elongate member defines the first retaining member.

8. The bone fixation wire of claim 1, wherein the retaining member comprises a separate member disposed on the elongate member.

9. The bone fixation wire of claim 1, wherein the first material comprises one of a metal and a metal alloy.

10. The bone fixation wire of claim 9, wherein the second material comprises a polymeric material.

11. The bone fixation wire of claim 1, wherein the elongate member comprises a cannula.

12. A bone fixation wire, comprising:
an elongate member having an elongate member first end defining a tip, an elongate member second end, and a lengthwise axis extending between the elongate member first end and the elongate member second end, the elongate member defining an outer wall extending between the elongate member first end and the elongate member second end;
the outer wall defining a first depression disposed on the elongate member outer wall between the elongate member first end and the geometric midpoint of the axial length of the elongate member on the lengthwise axis; and
a stopping member disposed on the elongate member, the stopping member having a stopping member first end, a stopping member second end, a stopping member outer surface, and a stopping member inner surface, the stopping member inner surface contacting the elongate member outer surface and defining a protrusion extending into the depression;
wherein the elongate member comprises a first material; and
wherein the stopping member comprises a second material that is different from the first material.

13. The bone fixation wire of claim 12, wherein the stopping member is disposed over the depression.

14. The bone fixation wire of claim 12, wherein the outer wall defines a second depression disposed between the elongate member first end and the geometric midpoint of the axial length of the elongate member on the lengthwise axis;
wherein the stopping member defines a second protrusion extending into the second depression; and
wherein the stopping member is disposed over the first and second depressions on the lengthwise axis of the elongate member.

15. The bone fixation wire of claim 14, wherein the first depression is disposed opposite the second depression with respect to the lengthwise axis of the elongate member.

16. The bone fixation wire of claim 12, wherein the first material comprises one of a metal and a metal alloy.

17. The bone fixation wire of claim 16, wherein the second material comprises a polymeric material.

18. The bone fixation wire of claim 12, wherein the elongate member comprises a cannula.

19. A bone fixation wire, comprising:
an elongate member having an elongate member first end defining a tip, an elongate member second end, and a lengthwise axis extending between the elongate member first end and the elongate member second end, the elongate member defining an outer wall extending between the elongate member first end and the elongate member second end;
the outer wall defining a first depression and a second depression, each of the first depression and the second depression disposed between the elongate member first end and the geometric midpoint of the axial length of the elongate member on the lengthwise axis, the first depression disposed opposite the second depression with respect to the lengthwise axis of the elongate member; and
a stopping member disposed on the elongate member, the stopping member having a stopping member first end, a stopping member second end, a stopping member outer surface, and a stopping member inner surface, the stopping member inner surface contacting the elongate member outer surface and defining a first protrusion extending into the first depression and a second protrusion extending into the second depression;
wherein the elongate member comprises one of a metal and a metal alloy; and
wherein the stopping member comprises a polymeric material.

20. The bone fixation wire of claim 19, wherein the elongate member comprises a cannula.

\* \* \* \* \*